United States Patent [19]

Carson et al.

[11] 4,284,352
[45] Aug. 18, 1981

[54] HEAT EXCHANGER FOR REFRACTOMETER

[75] Inventors: William W. Carson, Mendon; John S. Roe, Millis, both of Mass.

[73] Assignee: Waters Associates, Inc., Milford, Mass.

[21] Appl. No.: 50,326

[22] Filed: Jun. 20, 1979

[51] Int. Cl.³ .......................................... G01N 21/41
[52] U.S. Cl. ............................. 356/134; 73/61.1 R; 165/172
[58] Field of Search ............... 356/130, 131, 132, 134; 165/154, 164, 172, 176, DIG. 2; 73/61.1 R

[56] References Cited

U.S. PATENT DOCUMENTS

| | | | |
|---|---|---|---|
| 1,797,909 | 3/1931 | Ellsdorf | 165/DIG. 2 |
| 2,621,903 | 12/1952 | Cohler | 165/164 |
| 3,269,422 | 8/1966 | Matthews et al. | 165/172 |
| 3,522,725 | 8/1970 | Waters | 73/61.1 R |
| 3,539,263 | 11/1970 | Waters | 356/130 |
| 3,674,373 | 7/1972 | Waters et al. | 356/130 |
| 4,126,393 | 12/1978 | Sumikama et al. | 356/130 |

Primary Examiner—R. A. Rosenberger

[57] ABSTRACT

Apparatus for measuring changes in a physical property of a flowing fluid, including a cell through which the fluid flows, the cell having an inlet and an outlet, an inlet tube connected to the inlet of the cell, for delivering the flowing fluid to the cell, and an outlet tube connected to the outlet of the cell, for transporting the flowing fluid away from the cell, the inlet and outlet tubes being mounted in heat-exchanging relationship with each other, so as to transfer heat between the incoming and outgoing fluid and thereby reduce any temperature difference between the incoming fluid and the cell.

26 Claims, 15 Drawing Figures

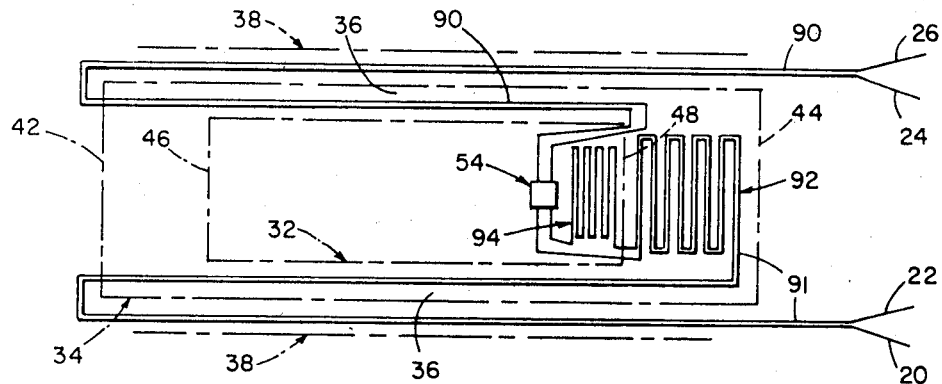
FIG 6
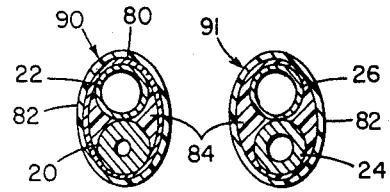
FIG 7a   FIG 7b
FIG 10a
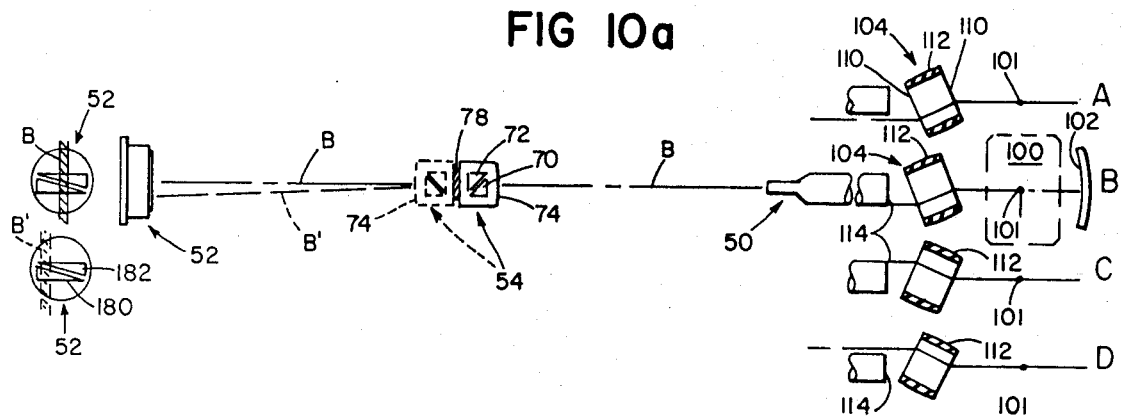
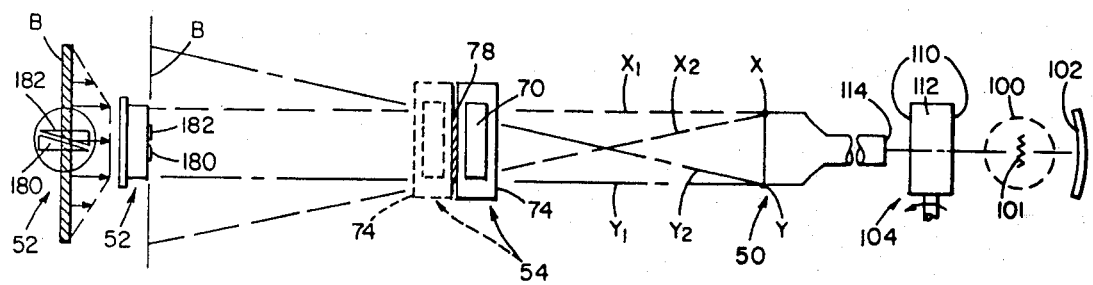
FIG 10b

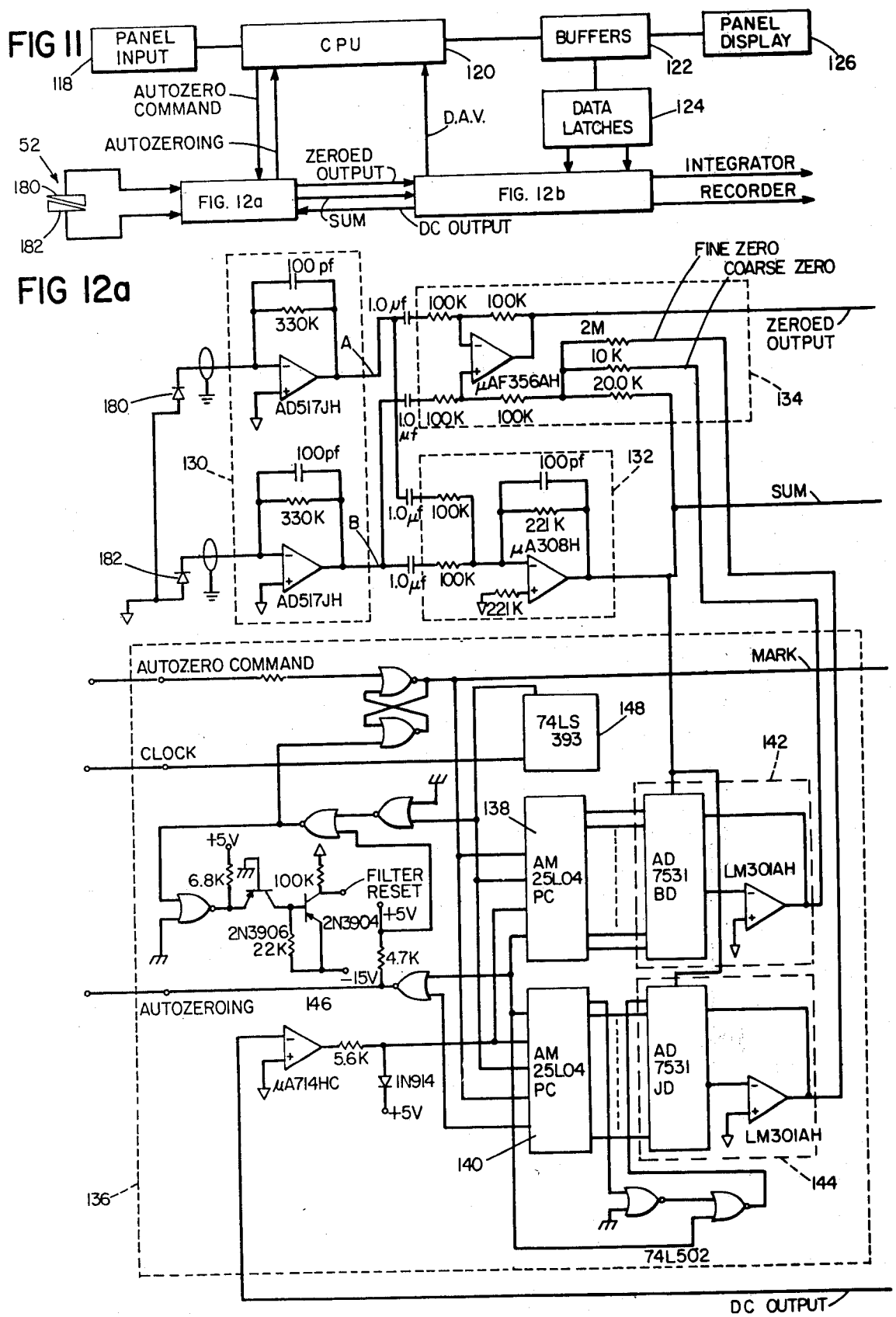

HEAT EXCHANGER FOR REFRACTOMETER

BACKGROUND OF THE INVENTION

This invention relates to devices which depend upon accurate measurement of changes in the refractivity of a flowing fluid, e.g., in liquid chromatography.

Because temperature affects refractivity, the temperature of the flowing liquid must be carefully controlled. Typically in refractive index detectors used in liquid chromatography the refractivities of sample and reference streams are compared at a cell. One technique for equalizing temperatures in the sample and reference streams in the cell has been to supply the fluid to the cell after having passed through sample and reference inlet tubes in heat-exchanging relationship with each other and with a large metal block. Ideally, both streams are at equal temperatures before entering the cell.

SUMMARY OF THE INVENTION

We have discovered that better control over temperature can be achieved with a heat-exchanging relationship between the sample inlet (to the cell) and sample outlet (from the cell) streams. The required hardware is simpler and inexpensive. Excellent temperature equalization of sample and reference fluids, and very fast warm up and cool down of the device, are made possible.

In preferred embodiments, inlet and outlet sample tubes run side-by-side in a counterflow relationship and are bonded together inside an epoxy-filled, heat-conductive braided tube; the cell is mounted inside an inner housing which is surrounded by an outer housing; the bonded pair extends through three heat exchange zones, one zone being outside the outer housing, another being along the insulating gap formed between the two housings, and another being a coil adjacent the cell and in a space between the housings; the inlet tube is coiled separately from the outlet tube at a location just upstream of the cell and inside the inner housing; the separate coil and the cell are in heat-exchanging relationship with a metallic member forming a thermal mass; a second pair of tubes also in counterflow heat-exchanging relationship supply a reference liquid to the cell; the refractivity of the two liquids is compared; and the inner housing is tubular and symmetrical about a plane perpendicular to the direction in which light is deflected.

PREFERRED EMBODIMENT

The structure and operation of a preferred embodiment of the invention will now be described, after first briefly describing the drawings.

DRAWINGS

FIG. 6 is a schematic of the heat exchanger plumbing.

FIGS. 7a and 7b are cross-sectional views through the sample and reference heat exchangers, respectively.

FIGS. 10a and 10b are diagrammatic views of the optical path through said embodiment.

FIG. 11 is a block diagram of the electronics that process the outputs of the photocells.

FIGS. 12a and 12b are schematics of the electronic circuits that null the photocell output and process the nulled output for display and integration.

STRUCTURE

Figure 1:
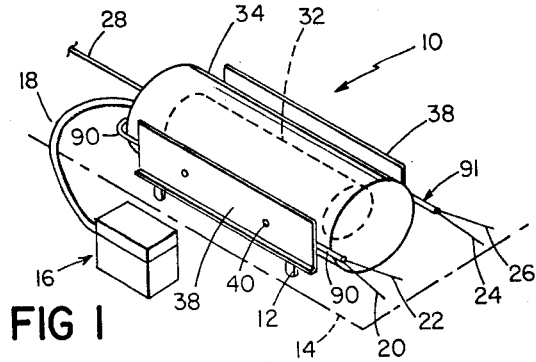
FIG. 1 is a perspective view of said embodiment.

Turning to FIG. 1, optical bench 10 is supported inside an oven on four insulating posts 12 attached to floor 14 of the oven. Light source 16 for the bench is positioned below the bench and outside of the oven. Fiber-optic cable 18 carries light from source 16 to the bench. Sample liquid from the outlet of a chromatographic column (not shown) positioned inside the oven flows into the optical bench through inlet tube 20 (0.009 inch ID), and out through outlet tube 22 (0.040 inch OD). A small diameter sample inlet tube is used to minimize band spreading in the chromatogram. Similarly, reference liquid flows into and out of the bench through inlet tube 24 (0.020 inch ID) and outlet tube 26 (0.040 inch OD). All four tubes are stainless steel and have 1/16 inch outside diameters. The outlet tubes have larger internal diameters than those of the inlets to lower backpressure and its effect on refractivity. Outlet tubes 22, 26 are connected together downstream of the optical bench to equalize sample and reference pressures at the flow cell. Electrical wires 28 from photocells 52 (FIG. 2) lead from the bench to processing circuits shown in FIGS. 11, 12a, and 12b.

Figure 2:
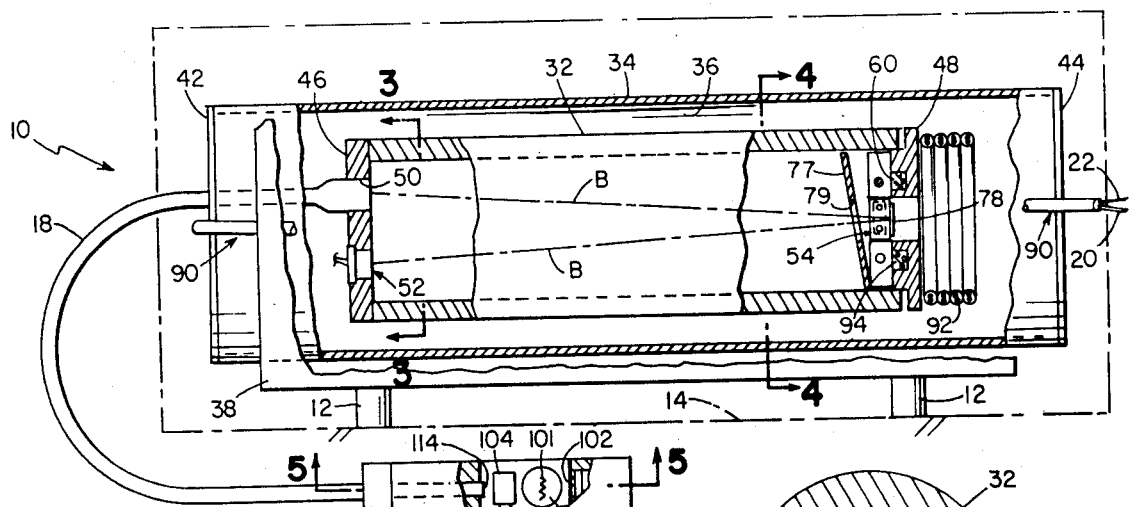
FIG. 2 is a partially cross-sectional view of said embodiment.
Figure 3:
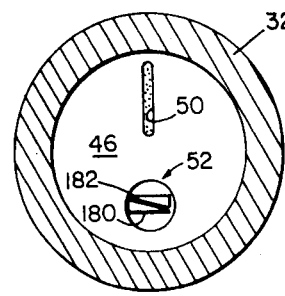
FIG. 3 is a cross-sectional view at 3—3 of FIG. 2, showing the photocell end of the optical bench.
Figure 4:
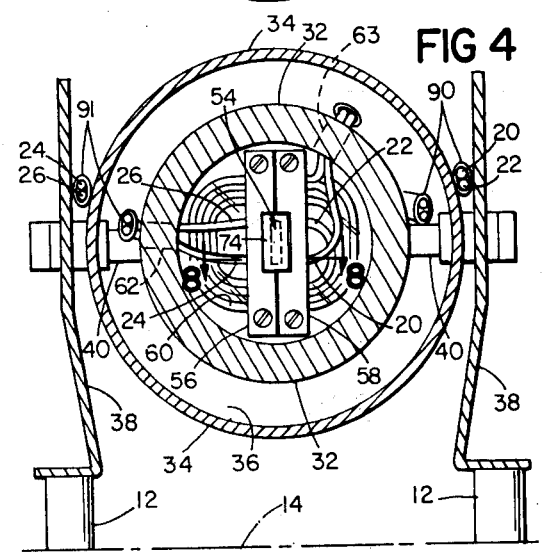
FIG. 4 is a cross-sectional view at 4—4 of FIG. 2, showing the flow cell end of the bench and the outer insulating cylinder and shields, with internal heat shield/light baffle 77 removed.

Turning to FIGS. 2 through 4, optical bench 10 consists of an inner cylinder 32, through which a light beam B is passed, and a concentric outer cylinder 34, which provides an insulating air gap 36. Two flat shields 38 (FIG. 1) retard radiation of heat to and from the bench, and act as legs (FIG. 4) to support the cylinders, via four bolts 40, on posts 12. End caps 42, 44 close each end of outer cylinder 34, and end caps 46, 48 each end of inner cylinder 32. End cap 46 supports elongated outlet 50 (0.050 inches wide by 0.35 inches high) of fiber-optic cable 18 and photocell 52. End cap 48 supports flow cell 54 via cell bridges 56, 58, which are attached to the cap and each other by screws and epoxy. Sample inlet and outlet tubes 20, 22 terminate at bridge 58; reference tubes 24, 26 terminate at bridge 56. Recess 60 in end cap 48 behind the bridges contains about four coils of sample inlet tube 20. Notches 62, 63 in inner cylinder 34 provide entryways for the tubes. The end caps, cylinders, and shields are all made from aluminum, to speed warm up of the bench while also insulating the bench by virtue of air gap 36 between the cylinders.

Figure 8:
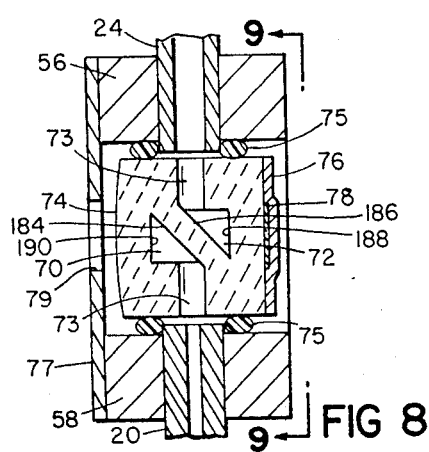
FIG. 8 is a cross-sectional view at 8—8 of FIG. 4, showing construction of the flow cell.
Figure 9:
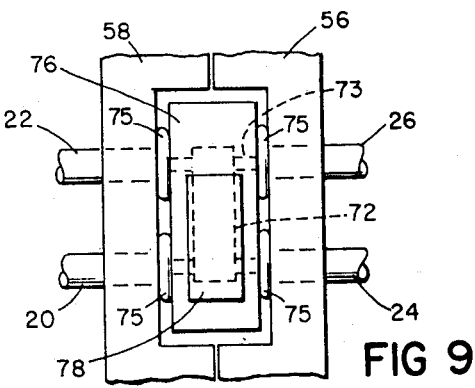
FIG. 9 is an elevation view of the back surface of the flow cell at 9—9 of FIG. 8.

Turning to FIGS. 8 and 9, flow cell 54 has two hollow chambers 70, 72, for the sample and reference liquids, respectively. Each chamber has a triangular (about 45×45×90 degrees, 0.062 inches on each short side) cross section (FIG. 8), and is connected to its respective inlet and outlet tubes by internal passages 73. The height (or vertical dimension in FIG. 9) of the chambers is about 0.50 inches. The flow cell is manufactured by fusing together, without adhesive, pieces of borosilicate glass. Teflon seals 75, compressed against the cell by the bridges, provide a seal between the sample and reference tubes and internal passages 73 of the cell. The front surface 74 of the flow cell is ground to provide an integral lens that has curvature in horizontal but not vertical planes. The back surface of the cell has a reflective surface coating 78 of gold to provide a mirror to reflect light back through chambers 70, 72 to photocell 52. The focal line of the lens is positioned at photocell 52, and the spacing between mirror 78 and photocell 52 is about 6.0 inches. As shown in FIG. 9, the mirror coating 78 is limited to approximately the area directly behind chamber 72, thereby to limit reflection principally to light passing through the triangular chambers. Other light is absorbed by black epoxy coating 76 applied over and around the mirror coating. The mirror coating is slightly larger than the chambers to accommodate variations in the internal size of chambers 70, 72. The coating stops short of the top of chambers 70, 72 (FIG. 9) so as not to reflect light passing through the top of the chambers, where bubbles might form.

To reduce radiant and convective heat transfer to the flow cell from within the optical bench, a blackened disk 77 with rectangular light-beam aperture 79 (just large enough to expose the flow cell) is positioned ahead of the flow cell. This disk also serves as a light baffle, and is tilted down 10° (FIG. 2).

Sample and reference liquid are brought into the flow cell through sample and reference counterflow heat exchangers 90, 91 (FIGS. 1, 6, and 7), each of which are formed by bonding corresponding inlet and outlet tubes together inside a tubular jacket. Each bonded pair is then routed along a multi-zone path beginning outside the bench and ending at the flow cell. As shown in FIG. 7, sample heat exchanger 90 is constructed by placing tubes 20, 22 inside a tubular copper braid 80, heat shrinking a polyethylene tube 82 over the outside of the copper braid, and filling the interstices between the braid and the inlet and outlet tubes with a low-viscosity, moderately-heat-conductive epoxy 84 (Stycast 3051). Reference tubes 24, 26 are bonded without a copper braid by inserting the tubes inside a Teflon tube and filling the tube with the same low-viscosity epoxy as used for the sample tubes. The braid is omitted because less efficient heat transfer is needed for the reference, as it does not flow during measurement, but only during flushing between measurements.

Turning to FIG. 6, the multi-zone path followed by the heat exchangers is shown diagrammatically. The first zone for both sample and reference heat exchangers begins outside the optical bench and extends along the outside length of the bench between outer cylinder 34 and shields 38 (total zone length about 8 inches). The sample heat exchanger 90 is positioned on the side of the bench closer to the center of the oven, where temperatures are better controlled. At end cap 42, both heat exchangers turn 180° and enter gap 36 between cylinders 32, 34, through a slot (not shown) in the end cap. The second zone for both sample and reference extends along gap 36 (total length about 7 inches). The reference heat exchanger goes directly from gap 36 into cylinder 32 through notch 62 in the end of cylinder. Inside cylinder 32, the reference inlet and outlet tubes are brought directly to flow cell 54 via bridge 56.

The sample heat exchanger 90 continues into a third zone beyond the end cap, where it is bent into coil 92, consisting of four turns (total coil length about 24 inches) positioned in the space behind end cap 48. The last coil is adjacent to the back of the end cap. From the coils the sample heat exchanger enters cylinder 32 through notch 63. Inside the cylinder, sample outlet tube 22 is connected directly to the flow cell. Sample inlet tube 20 is wound in another coil 94 (total length about 12 inches) before entering the flow cell. Coil 94 is positioned in recess 90, and potted with a heat-conductive epoxy to provide good conductivity with the end cap and cell bridges.

Figure 5:
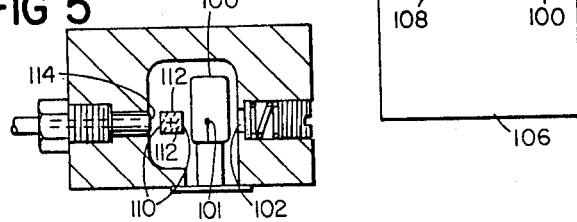
FIG. 5 is a cross-sectional view at 5—5 of FIG. 2, showing the light source.

Turning to FIGS. 2 and 5, light source 16 includes an incandescent bulb 100 (Phillips 6336, H3 base, 6 V, 55 W, operated at 4.8 V) with vertically-extending filament 101, a concave light-focusing mirror 102 (gold-coated glass), and a rotating prism 104. The prism is rotated at about 50 to 60 rpm along an axis parallel to the filament axis by a shaded-pole AC motor 106. The motor also drives a fan 108 which supplies cooling air to the bulb. Prism 104 is about 0.37 inches high, is made of glass, and has a rectangular cross section. Two opposite surfaces 110 of the prism are clear and about 0.3 inches wide. The other two surfaces 112 are opaqued with a white opaque silicone rubber, and are about 0.25 inches wide. Fiber-optic inlet 114 is round (about 0.150 inches in diameter) and is positioned opposite the prism from the bulb. Mirror 102 is positioned so as to focus an image of filament 101 on the face of inlet 114. Bulb 100 has a peak output in the near infra-red spectrum at a wavelength of about 1000 nanometers.

Fiber optic cable 18 is broken internally into sub-bundles and the sub-bundles are intentionally disordered at one end to randomize the light path between inlet 114 and outlet 50.

Photocell 52 has two adjacent triangular dual photovoltaic cells 180, 182 (gold-bonded silicon) arranged so that their long dimensions extend horizontally, which is the direction of movement of the light beam. Each triangle is about 0.150 inches long and 0.05 inches high. The spacing between the triangles is about 0.008 to 0.010 inches. The shunt impedance at operating temperature (about 150° C.) is maximized, as is the sensitivity to long wavelengths.

The oven in which the optical bench resides is heated by proportionally-controlled electrical resistance elements. Within the oven, temperatures can vary as much as 5° to 7° C. from point to point, but by much less (e.g., 0.3° C.) at the same point over time. The time period during which the resistance elements are on is varied in proportion to the difference between the actual oven temperature and the desired temperature and in proportion to the integral of this difference. To make oven temperature less sensitive to variations in AC line voltage, the time period is also made inversely proportional to the square of the line voltage, as the heat generated by the elements is proportional to the square of the line voltage. The elements are SCR controlled, and are turned on and off only at zero crossings of current.

Figure 12B:
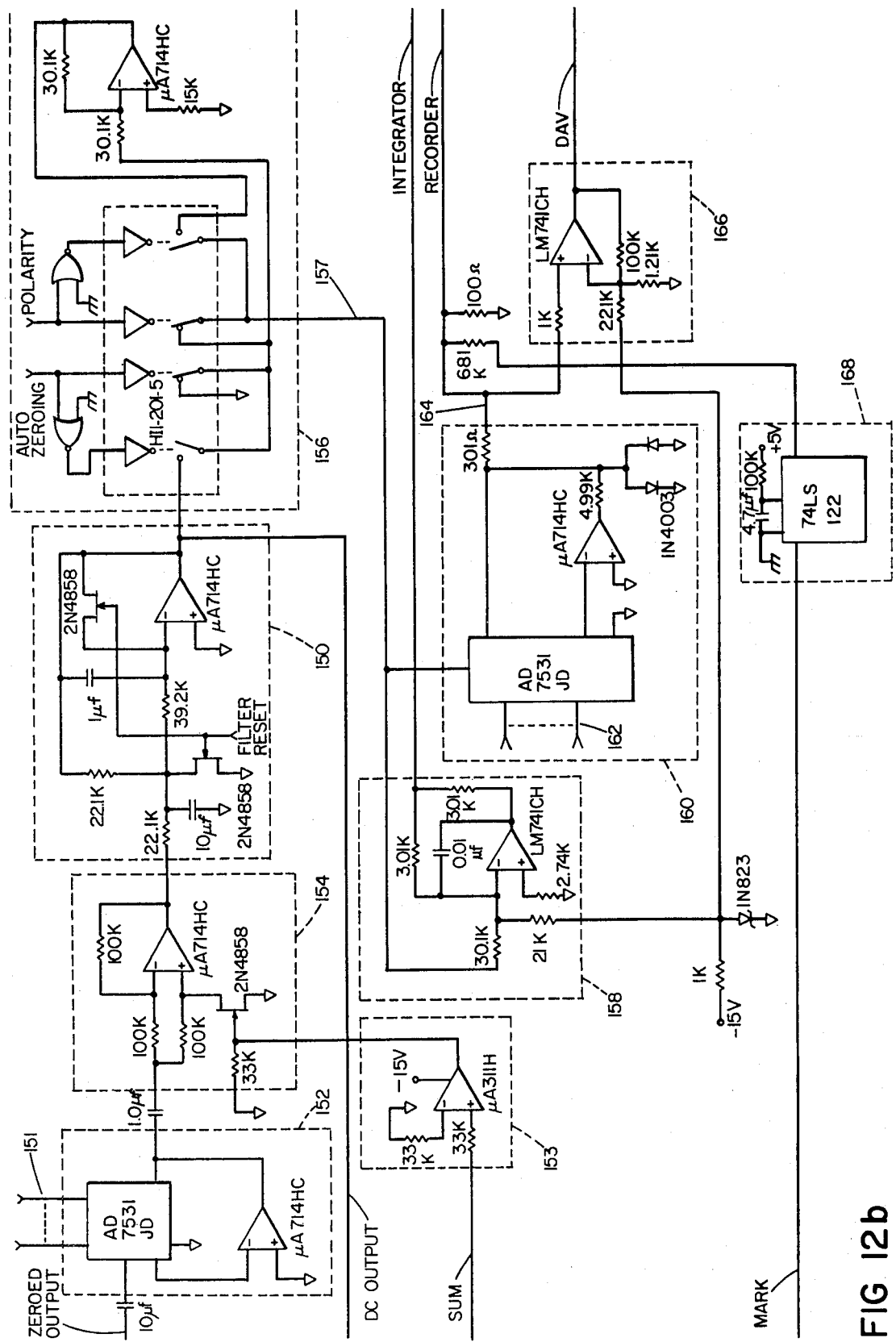

FIGS. 11, 12a, and 12b show the electrical circuits that process the outputs of photocell 52. FIG. 11 shows the overall circuitry in block diagram form. Panel inputs 118 (e.g., recorder gain) are fed to a central processor 120. The central processor (CPU) initiates the automatic electrical zeroing (nulling) of the photocell outputs, and sends signals via buffers 122 and gain latches 124 to circuitry shown in FIG. 12b to set the gain for display of the chromatogram on a recorder. An analog data acquisition voltage (D.A.V.) is converted to digital and sent by the processor via the input buffers to a panel display 126.

FIG. 12a shows the circuitry for electrical zeroing. The current outputs (AC signals) of photocells 180, 182 are brought via shielded cable to current-to-voltage converters 130. The AC voltages A, B produced by the converter are summed and amplified by a gain of 2.2 at amplifier 132, to form the expression $-2.2(A+B)$, which is called SUM. Amplifier 134 subtracts voltage A from voltage B, and adds to the difference the sum of three voltages: SUM, FINE ZERO, and COARSE ZERO. The latter two voltages are produced by multiplying SUM by a negative scale factor. Thus the output of amplifier 134 (ZEROED OUTPUT) can be expressed as $$[B-A]-2.2[0.33-0.67K_C-0.0033K_F][A+B]$$

where $K_C$ is the coarse zero scale factor and $K_F$ is the fine zero scale factor. Scale factors $K_C$, $K_F$ are set between about zero and about one by the digital circuitry of block 136, whenever a signal is sent across the AUTOZERO COMMAND lead. Normally zeroing would be done before a chromatogram was generated, but can be done at any time.

The above expression for the ZEROED OUTPUT can be presented in simplified form as $$(B-A)-K(A+B)$$

where K is the overall scale factor. The expression is independent of variations in the overall brightness of the light beam striking photocell 52 because the zeroing term $(K[A+B])$ is not a constant, but, like the difference term $(B-A)$ is proportional to beam brightness. For example, if the brightness were to rise by 10%, both the difference term and the zeroing term would similarly rise by 10%, and thus the whole expression would still remain equal to zero. When beam deflection does occur, as the result of refractivity changes, the zeroing term remains roughly constant because of the complementary shape of the two cells 180, 182, which at any horizontal location have roughly the same combined vertical height.

Two successive-approximation registers 138, 140 drive a pair of digital-to-analog converters 142, 144 to form the FINE ZERO and COARSE ZERO signals. Each of converters 142, 144 multiplies the SUM signal by a scale factor set by the digital output of registers 138, 140. Registers 138, 140 follow a conventional successive approximation algorithm to select the digital outputs or scale factors. About once a second, the registers receive a clock pulse from chip 148, which produces a slow clock from the much faster processor clock signal. At each clock pulse, the output of a register is adjusted in response to the output of comparator 146 which indicates whether the applied FINE/-COARSE ZERO signal is too large or too small. The input to comparator 146 is the DC OUTPUT, produced at filter amplifier 150 (FIG. 12b). A FILTER RESET connection between the zeroing circuitry and filter amplifier 150 is used during the zeroing process to discharge capacitors in the filter and reset the DC OUTPUT to zero. This allows for a more rapid autozero sequence. Register 138 works first to set the coarse scale factor $K_C$, and then register 140 to set the fine scale factor $K_F$. The AUTOZERO COMMAND is used by the CPU to start the autozero sequence. The AUTOZEROING signal is used to alert the central processor that the refractometer is autozeroing.

Turning to FIG. 12b, there is shown circuitry for processing the ZEROED OUTPUT. Amplifier 152 raises or lowers the signal level in response to command signals 151 from the central processor 120 via the data latch 124. Demodulator 154 (with the help of phase computing block 153) converts the AC signal to DC, and filter amplifier 150 smooths the DC signal. Switching block 156 operates during zeroing to turn off the RECORDER and INTEGRATOR signals. It also is used to change the polarity of the DC signal in response to a POLARITY signal from the central processor 120 via data latch 124. Downstream of block 156 the DC signal is processed by amplifier 158, and supplied to an integrator output lead. The DC signal is also processed by attenuator 160, under control of the central processor via signals 162. The attenuator produces a recorder output 164, which is supplied to a recorder output terminal and to amplifier 166, and a data acquisition voltage (D.A.V.), which is supplied to the central processor for panel display Block 168 supplies a mark signal for the recorder in response to the AUTOZERO COMMAND, to indicate on the chromatogram the point at which the sample injection occurs. The CPU issues the AUTOZERO COMMAND at the time of sample injection.

OPERATION

In operation, the oven surrounding the optical bench and chromatographic column is turned on, and about an hour and one half warm up period is allowed for temperature equalization within the bench. After warm up, solvent is pumped through the sample and reference circuits within the bench. When solvents are changed, sufficient time is allowed for flushing both circuits. Flow is then stopped in the reference circuit (but reference chamber 72 remains filled with reference liquid). A sample is then injected into the sample column. The electrical output of the refractometer is zeroed by initiating the automatic zeroing sequence described above. Sample passes through the chromatographic column and into the optical bench. Generally speaking, variations in refractivity of the sample cause movement of the light beam with respect to photocell 52, and thereby changed the electrical output, which is plotted against time on a chart recorder, producing a chromatogram.

Temperatures within chambers 70, 72 of the flow cell are maintained within about 0.0001° C. of each other during operation to minimize error. A temperature difference between the two flow cell chambers results in a refractivity difference. Temperature equalization is achieved by providing good thermal insulation around the flow cell, in the form of air gap 36 between the inner and outer cylinders, shields 38, and blackened disk 77; surrounding the flow cell with a thermal mass, in the form of bridges 56, 58 and end cap 48; and directing incoming sample flow through a very efficient counter-flow heat exchanger to bring the temperature of the sample to the flow cell temperature. Incoming sample upstream of the heat exchanger is typically as much as 1° C. (and possibly 2° to 3° C.) different in temperature than the flow cell because of spatial differences in oven temperature and because of heat generated by viscous heating inside the inlet tube. This difference in temperature is gradually reduced along the length of the heat exchanger by thermal conduction between the inlet and outlet tubes. At the end of the heat exchanger, whatever very small temperature difference remains is minimized by heat transfer between end cap 48 and coil 94 just prior to entry into the flow cell.

The sample heat exchanger is divided into three zones to improve its efficiency, with each successive zone being more thermally stable and closer to the temperature of the flow cell. The construction of the heat exchanger provides good thermal conduction between tubes but very low conduction along the flow direction of the tubes. There is significant heat transfer between the tubes and the surrounding air; thus thermal interaction between the heat exchanger and the region surrounding it must be considered. The first zone, between outer cylinder 34 and shield 38, provides a gradual approach in temperature before the heat exchanger enters the optical bench. The length of this zone is greater than 10% of the length of the sample inlet tube within the bench. Without the first zone, i.e., if the inlet and outlet tubes were joined just outside the entry to end cap 42, there would be a steeper approach in temperature along the heat exchanger, and much of this approach in temperature would occur along portions of the heat exchanger inside air gap 36, thereby undesirably transferring heat to or from the bench. With the preferred arrangement of a first zone outside the bench, the heat exchanger temperature is closer to that of the bench when entering the air gap.

The heat exchanger enters the gap at the photocell end of the bench, thereby assuring that whatever heat transfer to or from the bench does occur is at a location well separated from the flow cell.

This same concept of routing the heat exchanger through increasingly more thermally stable regions is also applied to the second and third zones. In the second zone, the sample heat exchanger is directed along air gap 36 from the photocell end to the flow cell end, where temperature stability is highest. In the third zone, the sample heat exchanger is coiled behind the flow cell end cap, with each successive coil being closer to the end cap and flow cell.

As a final step, the sample inlet tube alone is coiled in recess 60 of end cap 48 to minimize whatever small temperature difference remains between the incoming sample and the flow cell.

Because the reference solvent does not flow during a measurement, the reference heat exchanger is less sophisticated. It lacks the third coiled zone, and has no copper, heat-conductive braid to surround inlet and outlet tubes. Limited heat exchange is provided on the reference side to maintain rough temperature equalization during flushing of the reference circuit thereby shortening the period needed to stabilize temperatures after flushing.

The optical elements of the refractometer are shown diagrammatically in FIGS. 10a and 10b. For clarity the optical path is shown unfolded, with mirror 78 treated as a window. FIG. 10a shows a horizontal section through the optical path; FIG. 10b shows a vertical section.

Turning to FIG. 10a, a single light ray B is shown to illustrate beam movements. Lens surface 74 on flow cell 54 focuses the light emerging from fiber-optic cable outlet 50 onto photocell 52. The focused image on the photocell is shown diagrammatically in the views on the left side of the Figure. To illustrate the effect caused by rotation of prism 104, four views (A through D) of the prism in different angular positions are shown along with the corresponding positions of the light beam on the photocell.

Light passing through chambers 70, 72 is bent in proportion to the difference in the refractive index of the liquids in the two chambers. Referring to FIG. 8, the chambers are conventionally constructed so that surface 190 in chamber 70 is parallel to surface 188 in chamber 72 and, similarly, so that surfaces 184 and 186 are parallel. These four surfaces are the four at which light is bent by refraction. If the liquid of the same refractive index is in both chambers, light will be bent by the same amount at each of the corresponding parallel surfaces, and will emerge from the flow cell along a path B which is unaffected by changes in refractivity common to both chambers. If liquid in the two chambers differs in refractive index, light will be bent differentially at these parallel surfaces, and will emerge along a path skewed from the equal-refractivity path. Such a condition is illustrated in FIG. 10a by light ray B'. The amount by which the light beam is skewed or bent at the flow cell is measured by detecting the position of the image of the beam at photocell 52. The difference between the electrical outputs of the two triangular cells 180, 182 can very finely resolve the horizontal position of the light beam. Imperfections in alignment of the photocell with the flow cell and other tolerances in the system typically cause these electrical outputs of the two cells to be unequal even when sample and reference liquids have the same refractive index. This initial electrical difference is nulled by the automatic zeroing procedure described above.

Ideally, the light beam location on the photocell 52 should only be a function of the difference in refractive index between sample and reference (and not a function of the location of bulb filament 101). To achieve this, the light intensity distribution across the fiber optic outlet 50 must be spatially stable over the time period of chromatographic interest (1 second to several hours). This requires that the light intensity distribution into the fiber optics be stable. As viewed from the fiber optics inlet 114, the apparent position of bulb filament 101 varies due to filament distortion and thermal eddies in the air path between the filament and the inlet. Filament movements along the length of the filament (vertical in FIG. 2) are relatively noncritical. Similarly, changes in the filament distance from the fiber optics inlet are not observable and thus are noncritical. Along the third axis of movement (vertical in FIG. 5) the apparent filament location as viewed by the fiber optics inlet must be spatially stabilized for the beam location at the photocell to be independent of filament location. To achieve stabilization, a Spatially Homogenizing Optical Modulator (SHOM) in the form of rectangular prism 104 is employed in the light path between the filament and the fiber optics inlet. The prism provides an optical path offset which is a function of its rotation position. When the prism rotates, the filament optically appears to sweep across the face of the fiber optics inlet 114. In position A, the prism is so oriented that the light from filament 101 is bent outside the acceptance angle of the fibers in cable 18, and negligible light is transmitted to the bench. In position B, the prism has rotated sufficiently for light to be transmitted through at least some of the fibers in the cable. In position C, the prism has swept the filament image across the face of the fiber optics inlet. In position D, the prism has moved the image to a position beyond the acceptance angle of the fibers, and again negligible light is transmitted. As the prism rotates further, the beam first reappears beyond the acceptance angle of the fibers, as in position A, and then another sweep begins. The sweeping action, including the period of negligible light transmission, occurs two times during each revolution of the prism, or about 100 times per second.

If filament 101 moves or appears to move, this has the effect of changing the time at which the beam starts and finishes its sweep across the fiber optics inlet. That is, only the phase of the beam movement is altered by movement of the filament. The electronics described above compute the average or middle position swept by the image. The electronics are insensitive to such phase or time shifts, and thus the undesirable effects of filament shift are minimized.

The apparent light source position is further stabilized by using the randomized fiber optics bundle 18. In a prefectly randomized fiber optics bundle, adjacent fibers at one end of the bundle are randomly distributed at the other end. Therefore, increasing the light on one side of the bundle input while decreasing it on the other side results in no change in the light distribution across the fiber optics output end. In actual practice, the randomization in a bundle is not perfect, and some change does occur at the output end. But using the randomized fiber optics does further decrease the effect of filament motion on beam movement at photocell 52.

As can be seen in FIG. 10b, the optics do not focus the beam onto the photocell in the vertical direction, as done in the horizontal direction. Instead, light emerging from outlet 50 of cable 18 remains unfocused in vertical planes, thereby producing for each point of light at the outlet a vertical line of light at the photocell. The vertical height of this line is limited by the vertical height of mirror 78, which acts as a mask. Light rays from individual points, e.g., points X and Y, on the cable outlet 50 fan out, but only rays inside of limit rays $X_1$, $X_2$ ($Y_1$, $Y_2$ for point Y) reach the photocell. (Other rays are not reflected through the photocell). The vertical heights of mirror 78, photocell 52, and cable outlet 50 and the spacing between the flow cell and photocell ends of the bench are all selected so that the limit rays for all points on the cable outlet strike fully above and fully below triangular cells 180, 182 of the photocell. Limit rays for point X and point Y, at the top and bottom extremities of the cable outlet, are shown in FIG. 10b. Thus each point on the cable outlet produces a line of uniform intensity at the photocell. And these lines all overlap over the photocell, thereby assuring a uniform vertical intensity across the photocell no matter what vertical variation in intensity may exist at the cable outlet (e.g., due to variation in filament intensity in the vertical direction). The end result is the light intensity profile shown at the left side of FIG. 10b. Across the vertical height of the photocells the intensity is uniform; outside the photocells the intensity falls off to zero. Vertical uniformity of light intensity at the photocells is needed to linearly determine the horizontal light beam location on the triangular-shaped cells 180, 182. (A vertical variation in intensity would be indistinguishable from a horizontal movement of the light beam.)

OTHER EMBODIMENTS

Other embodiments of the invention are within the following claims. For example, the heat exchanger of the invention could usefully be placed in front of or combined with prior art devices that use a large metal block as a thermal mass, in applications that do not require fast warm up (e.g., room temperature refractometers). In these instances, the bonded inlet and outlet tubes could be placed in front of or extend through the metal block.

Further, fewer heat-exchang zones could be used, particularly if the bench, cell, and heat exchanger were better insulated. And with the preferred arrangement of three zones for the sample, other zone arrangements could be used. For example, the heat exchanger could be coiled in the second zone in gap 36, and the first zone could be located elsewhere than the space between shields 38 and cylinder 34.

Still further, the reference and sample circuits could be reversed so as to allow the same refractometer to be used for both analytical and preparative chromotography. In analytical chromatography (the described embodiment), a small volume of sample flows at high pressure and low flow rate. In preparative chromatography, a larger volume of sample flows at lower pressure and higher flow rate. Sample concentration is generally much greater in preparative work. These differences have conventionally required that different refractometers be used for each type system. By making the sample and reference inlet tubes of different diameter tubing (e.g., 9 mils and 20 mils I.D.), the sample can be fed through the small line for analytical (described embodiment) and through the large line for preparative, thereby accommodating different flow rates and pressures. Further, the very large dynamic range (ability to accurately measure concentration variations over a very large range of concentrations) of the refractometer is large enough to encompass sample concentrations of both preparative and analytical systems.

OTHER INVENTIONS

Subject matter relating to the integral mirror coating on the flow cell was the invention of Larry J. Finn (Ser. No. 51,810 filed June 25, 1979).

Subject matter relating to the integral lensing surface on the flow cell (Ser. No. 51,811 filed June 25, 1979), the rotating prism, and the unfocused optics in vertical planes (the latter two corresponding to Ser. No. 51,812 filed June 25, 1979) were the sole inventions of William W. Carson.

Subject matter relating to zeroing the photocell output was the joint invention of William W. Carson and Norman F. Rolfe (Ser. No. 51,809 filed June 25, 1979).

Subject matter relating to resetting the filter during autozeroing was the invention of Norman F. Rolfe (Ser. No. 59,292 filed July 20, 1979).

What is claimed is:

1. Apparatus for measuring changes in a physical property of a flowing fluid, comprising
    a cell through which said fluid flows, said cell having an inlet and an outlet,
    an inlet tube connected to the inlet of said cell, for delivering said flowing fluid to said cell, and
    an outlet tube connected to the outlet of said cell, for transporting said flowing fluid away from said cell,
    said inlet and outlet tubes being mounted in heat-exchanging relationship with each other, so as to transfer heat between the incoming and outgoing fluid and thereby reduce any temperature difference between the incoming fluid and the cell.

2. The apparatus of claim 1 wherein said physical property is refractivity and said fluid flowing through said inlet and outlet tubes is a sample fluid.

3. The apparatus of claim 1 or 2 wherein said tubes extend side-by-side in a counterflow relationship to cause the temperatures of fluid flowing through said inlet tube to increasingly approach the temperature of said cell through at least a first heat-exchange zone.

4. The apparatus of claim 3 wherein said cell is mounted inside a housing and said first zone is inside said housing.

5. The apparatus of claim 4 wherein said tubes extend through at least a second heat-exchange zone upstream of said first zone, said second zone being inside said housing.

6. The apparatus of claim 5 wherein said tubes extend through a third heat-exchange zone outside said housing.

7. The apparatus of claim 6 wherein inside said housing is a second housing in which is mounted said cell and said tubes are coiled in said first zone outside said second housing.

8. The apparatus of claim 6 wherein inside said housing is a second housing in which is mounted said cell, and said inlet tube is coiled separately from said outlet tube inside said second housing.

9. The apparatus of claim 8 further comprising a metallic member forming a thermal mass with which said cell and said separate coil are in heat-exchanging relationship.

10. The apparatus of claim 5 further comprising a second housing inside of said first-mentioned housing and wherein said second zone is in the space between said first-mentioned housing and said second housing.

11. The apparatus of claim 10 wherein said first and second housings respectively comprise outer and inner tubular members and the gap between said tubular members forms an insulating air gap through which said second zone extends.

12. The apparatus of claim 11 wherein said cell is positioned at one end of said inner tubular member and the upstream end of said second zone begins at the end of said gap opposite said flow cell end.

13. The apparatus of claim 11 further comprising means for retarding radiant heat transfer from said outer tubular member, said means comprising at least one sheet member spaced from said outer member and said third zone extending along the space between said sheet member and said outer tubular member.

14. The apparatus of claim 4 wherein said first zone is at least 10 percent of the total length of said inlet tube downstream of said first zone.

15. The apparatus of claim 4 wherein said housing includes an inner tubular member containing said cell and said tubular member is symmetrical about a plane perpendicular to the plane in which light is deflected in said apparatus, whereby said tubular member is less susceptible to bending in response to changes in temperature of said apparatus.

16. The apparatus of claim 3 wherein said tubes are encased in a heat conductive member.

17. The apparatus of claim 16 wherein said member includes a metallic tubular member surrounding said tubes.

18. The apparatus of claim 17 wherein said tubular member is a braided tube and the interstices between said braided tube and said inlet and outlet tubes are filled with a heat conducting material.

19. The apparatus of claim 18 wherein said material is an epoxy.

20. The apparatus of claim 3 wherein said tubes extend through first and second zones before reaching said cell and said tubes are in heat-exchanging relationship with respectively first and second regions of said apparatus surrounding said zones, said inlet tube passing first through said second zone and then through said first zone, and wherein said improvement comprises means for keeping the temperature of said first region closer to said flow cell temperature than is the temperature of said second region.

21. The apparatus of claim 20 wherein said first region is an enclosed air space adjacent said cell and said second region is an enclosed air space further away from said cell.

22. The apparatus of claim 3, wherein said side-by-side tubes are in heat-exchanging relationship with air within said apparatus.

23. The apparatus of claim 1 or 2 wherein at least one of said tubes is coiled.

24. The apparatus of claim 2 further comprising second inlet and outlet tubes for respectively carrying reference fluid to and from said cell, and means for comparing the refractivities of said sample and reference liquids, said improvement further comprising the mounting of said second tubes in counterflow heat-exchanging relationship with each other to cause the temperature of fluid flowing in the reference inlet tube to increasingly approach the temperature of said cell.

25. The apparatus of claim 24 wherein said reference inlet tube is sufficiently larger than said sample inlet tube and the measurement range of said apparatus is sufficiently great to allow said apparatus to be used for both analytical and preparative chromatography by flowing sample through said sample inlet for analytical and through said reference inlet for preparative.

26. The apparatus of claim 1 or 2 further comprising means for thermally isolating said cell and means for providing a thermal mass in the vicinity of said flow cell and in heat-exchanging relationship with said cell, whereby said cell is held at a stable temperature by said insulation and thermal mass means and the temperature of said sample inlet stream is caused to approach this stable cell temperature by said counterflow heat-exchanging relationship between said inlet and outlet tubes.

* * * * *